United States Patent [19]

Hofer et al.

[11] 4,058,525
[45] Nov. 15, 1977

[54] 4-AMINO-5-THIONE-1,2,4-TRIAZINES

[75] Inventors: Wolfgang Hofer; Fritz Maurer; Hans-Jochem Riebel; Lothar Rohe, all of Wuppertal; Ludwig Eue, Leverkusen; Robert R. Schmidt, Cologne, all of Germany

[73] Assignee: Bayer Aktiengesellschaft, Leverkusen, Germany

[21] Appl. No.: 670,911

[22] Filed: Mar. 26, 1976

[30] Foreign Application Priority Data

Apr. 22, 1975 Germany .............................. 2517654

[51] Int. Cl.² .......................................... C07D 253/06
[52] U.S. Cl. ......................................... 544/182; 71/93
[58] Field of Search ...................... 260/248 AS; 71/93

[56] References Cited
U.S. PATENT DOCUMENTS

| | | | |
|---|---|---|---|
| 3,505,057 | 4/1970 | Luckenbaugh | 71/93 |
| 3,671,523 | 6/1972 | Westphal et al. | 260/248 |
| 3,961,936 | 6/1976 | Westphal et al. | 71/93 |

Primary Examiner—John M. Ford

Attorney, Agent, or Firm—Burgess, Dinklage & Sprung

[57] ABSTRACT

The invention provides new 4-amino-5-thione-1,2,4-triazine (4,5-H) of the formula

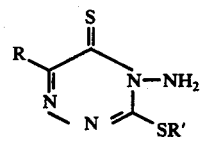

in which
R is alkyl of up to 8 carbon atoms, cycloalkyl of from 5 to 7 carbon atoms, cycloalkenyl of from 5 to 7 carbon atoms, phenyl, which can optionally be mono-substituted or polysubstituted by halogen, or alkoxyalkyl of from 1 to 4 carbon atoms per alkyl and alkoxy moiety, and
R' is hydrogen or alkyl of up to 4 carbon atoms;

which are outstandingly effective as herbicides, particularly as selective herbicides.

14 Claims, No Drawings

4-AMINO-5-THIONE-1,2,4-TRIAZINES

This invention relates to certain new 4-amino-5-thione-1,2,4-triazine compounds, herbicidal compositions containing them and to their use as herbicides.

It is known that 4-ethylamino-2-tert.-butylamino-6-methylthio-1,3,5-triazine (compare U.S. Pat. No. 2,909,420) can be used to combat weeds. However, this compound is not active against all weeds, particularly if low amounts and low concentrations are used; for example, its activity against species of Echinochloa is low.

The present invention provides 4-amino-5-thione-1,2,4-triazines (4,5-H) of the formula $$\begin{array}{c} S \\ R \diagdown \diagup \\ \diagup N-NH_2 \\ N \diagdown \diagup \\ N \diagup SR' \end{array} \qquad (I),$$

in which
R is alkyl of up to 8 carbon atoms, cycloalkyl of from 5 to 7 carbon atoms, cycloalkenyl of from 5 to 7 carbon atoms, phenyl, which can optionally be mono-substituted or polysubstituted by halogen, or alkoxyalkyl of from 1 to 4 carbon atoms per alkyl and alkoxy moiety, and
R' is hydrogen or alkyl of up to 4 carbon atoms.

Preferably, R represents straight-chain or branched alkyl of from 1 to 7 carbon atoms, cyclohexyl, cyclohexenyl, methoxymethyl, ethoxymethyl, n-propoxymethyl, methoxyethyl, ethoxyethyl, phenyl or chlorophenyl, especially 2- or 4-chlorophenyl, 2,4-dichlorophenyl, 2,4,6-trichlorophenyl or 3,4-dichlorophenyl; and R' represents hydrogen or straight-chain or branched alkyl of from 1 to 3 carbon atoms.

The invention also provides a process for the production of a 4-amino-5-thione-1,2,4-triazine (4,5-H) of the formula (I) in which a. an α-keto-thiocarboxylic acid amide of the formula $$R-CO-CS-N \diagup{R_1} \diagdown{R_2} \qquad (II)$$

in which
R has the abovementioned meaning and
$R_1$ and $R_2$, which can be identical or different, represent hydrogen or optionally substituted alkyl,
is reacted with a thiocarbohydrazide of the formula $$H_2N-NH-\underset{\underset{SR'}{|}}{C}=N-NH_2 \; (x \; HX) \qquad (III)$$

in which
R' has the abovementioned meaning and
X represents halogen,
optionally in the presence of an acid and optionally in the presence of a solvent; or b. a 4-amino-5-oxo-1,2,4-triazine(4,5-H) derivative of the formula $$\begin{array}{c} O \\ R \diagdown \diagup \\ \diagup N-NH_2 \\ N \diagdown \diagup \\ N \diagup SR' \end{array} \qquad (IV)$$

in which
R and R' have the above-meanings
is reacted with a sulfurizing agent, such as phosphorus pentasulfide, optionally in the presence of a solvent; or c. (if the compound to be prepared is one of formula (I) in which R' represents alkyl of up to 4 carbon atoms) there is prepared according to process variant (a) or (b), the 4-amino-3-mercapto-5-thione-1,2,4-triazine (4,5-H) of the formula $$\begin{array}{c} S \\ R \diagdown \diagup \\ \diagup N-NH_2 \\ N \diagdown \diagup \\ N \diagup SH \end{array} \qquad (V),$$

in which
R has the above-mentioned meaning
and this is reacted with an alkyl halide of the formula $$R''-X \qquad (VI),$$

in which
R'' is alkyl of from 1 to 4 carbon atoms and
X is halogen,
optionally in the presence of an acid acceptor and optionally in the presence of a solvent.

Surprisingly, the 4-amino-5-thione-1,2,4-triazines-(4,5-H) according to the invention exhibit a substantially greater herbicidal action than the closely related 4-ethylamino-2-tert.-butylamino-6-methylthio-1,3,5-triazine, previously known in the art. The compounds according to the invention are markedly more active against weeds and thus represent a genuine enrichment of the art.

If, using process variant (a), 2,4-dichlorophenyl-glyoxylic acid N-(3-morpholino-propyl)-thioamide hydrobromide and S-n-propylthiocarbohydrazide hydrobromide are used as starting materials, or, using process variant (b), 4-amino-3-mercapto-6-methyl-5-oxo-1,2,4-triazine(4,5-H) and phosphorus pentasulfide are used as starting materials and, using process variant (c), 4-amino-3-mercapto-5-thione-6-ethyl-1,2,4-triazine (4,5-H) and methyl iodide are used as starting materials, the course of the reactions can be represented by the following formula schemes:

(a)

Cl—⌬—CO—CS—NH—CH₂—CH₂—CH₂—N⌬O x HBr

+ $H_2N-NH-\underset{\underset{SC_3H_7-n}{|}}{C}=N-NH_2 \times HBr \xrightarrow{[Acid]}$ Cl—⌬—C(=N...)—C(=S)—N-NH₂, SC₃H₇-n -continued

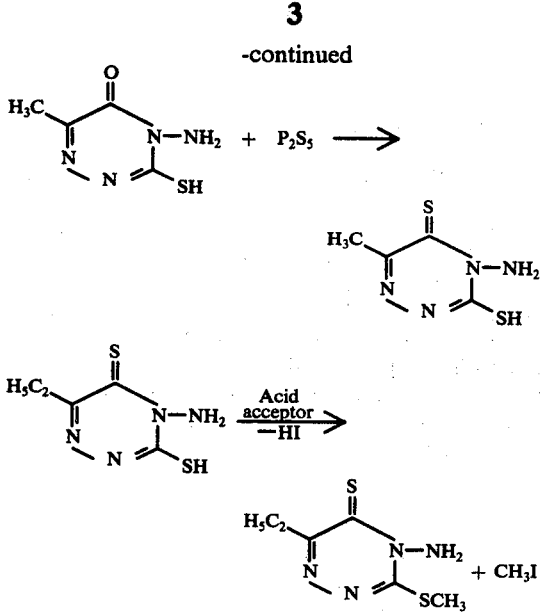

The α-keto-thiocarboxylic acid amides which can be used as starting materials for process variant (a) are defined by the general formula (II). In this formula, $R_1$ and $R_2$ preferably represent hydrogen, straight-chain or branched alkyl or substituted alkyl, for example morpholino-alkyl, and R has the preferred meanings already mentioned above.

The majority of the α-keto-thiocarboxylic acid amides of the formula (II) are known and can be prepared in accordance with generally known methods which are described in the literature, for example from haloalkyl ketones with amines in the presence of sulfur (compare Liebigs Ann. Chem. 691, pages 92–108 (1966) or from carboxylic acid halides with alkyl isonitriles, followed by reaction with hydrogen sulfide (compare Chem. Ber 94, page 1121 (1961)). Detailed illustrations thereof are given in the Examples hereinbelow.

The following may be mentioned as examples of the α-keto-thiocarboxylic acid amides: 2-chlorophenyl-, 4-chlorophenyl-, 2,4-dichlorophenyl-, 3,4-dichlorophenyl-, 2,4,6-trichlorophenyl-, cyclohexyl-, cyclohex-3-enyl- and phenylglyoxylic acid N-(3-morpholinopropyl)-thioamide hydrohalide, pyruvic acid N-n-butyl-thioamide, methyl-, dimethyl- and trimethyl-pyruvic acid N-n-butylthioamide, methoxy and ethoxy-pyruvic acid N-nbutylthioamide and N-(3-morpholinopropyl)-thioamide, iso-propylpyruvic acid N-(3-morpholino-propyl-thioamide, iso-propylpyruvic acid N-(3-morpholinopropyl)-thioamide, ethyl-n-butyl-pyruvic acid N-(3-morpholinopropyl)-thioamide and ethyl-n-propyl-pyruvic acid N-(3-morpholinopropyl)-thioamide.

The thiocarbohydrazide which can be used as starting material for process variant (a) and the S-alkylthiocarbohydrazides are defined by the general formula (III). R' has the preferred meanings already mentioned above.

The thiocarbohydrazides are known from the literature and can be prepared in accordance with generally known methods.

The following may be mentioned as examples of the thiocarbohydrazides: thiocarbohydrazide S-methyl-, S-ethyl-, S-n-propyl- and S-iso-propyl-thiocarbohydrazide.

The 4-amino-5-oxo-1,2,4-triazine(4,5-H) derivatives to be used as starting materials for process variant (b) are generally defined by the formula (IV). R and R' have the preferred meanings already mentioned earlier. The compounds are known and can be prepared in accordance with generally known methods.

The following may be mentioned as examples of these derivatives: 6-methyl-, 6-ethyl-, 6-n-propyl-, 6-iso-propyl-, 6-n-butyl-, 6-iso-butyl-, 6-tert.-butyl-, 6-sec.-butyl-, 6-n-pentyl-, 6-n-hexyl-, 6-n-heptyl, 6-iso-pentyl-, 6-neopentyl-, 6-(2-ethyl-pentyl)-, 6-(2,3-dimethyl-butyl-, 6-(2,4-dimethyl-pentyl)-, 6-(2,2,4-trimethyl-pentyl)-, 6-cyclohexyl-, 6-cyclohex-3-enyl-, 6-phenyl-, 6-(2-chlorophenyl)-, 6-(2,4-dichlorophenyl)-, 6-(2,4,6-trichlorophenyl)-, 6-(3,4-dichlorophenyl)-, 6-methoxymethyl-, 6-methoxyethyl-, 6-ethoxymethyl-, 6-ethoxyethyl-, 6-n-propoxymethyl-, 6-iso-propoxymethyl-, 6-n-propoxyethyl- and 6-iso-propoxyethyl-4-amino-3-mercapto-5-oxo-1,2,4-triazine(4,5-H) as well as the corresponding 3-methylthio-, 3-ethylthio-, 3-n-propylthio and 3-iso-propylthio derivatives.

The 4-amino-3-mercapto-5-thione-1,2,4-triazine derivatives to be used as starting materials for the process according to process variant (c) are generally defined by the formula (V). R has the preferred meanings already mentioned earlier. The compounds are not previously known but can be prepared in accordance with the methods described herein, for example from α-keto-thiocarboxylic acid amides (II) and thiocarbohydrazides (III) (compare process variant (a)).

The following may be mentioned individually as examples of these derivatives: 6-methyl-, 6-ethyl-, 6-n-propyl-, 6-iso-propyl-, 6-n-butyl-, 6-iso-butyl-, 6-tert.-butyl-, 6-sec.-butyl-, 6-n-pentyl-, 6-n-hexyl-, 5-n-heptyl-, 6-iso-pentyl-, 6-neopentyl-, 6-(2-ethyl-pentyl-, 6-(2,3-dimethyl-butyl)- 6-(2,4-dimethyl-pentyl)-, 6-(2,2,4-trimethyl-pentyl)-, 6-cyclohexyl-, 6-cyclohex-3-enyl-, 6-phenyl-, 6-(2-chlorophenyl)-, 6-(2,4-dichlorophenyl)-, 6-(2,4,6-trichlorophenyl)-, 6-(3,4-dichlorophenyl)-, 6-methoxymethyl-, 6-methoxyethyl-, 6-ethoxymethyl-, 6-ethoxyethyl-, 6-n-propoxymethyl-, 6-iso-propoxymethyl-, 6-n-propoxyethyl- and 6-isopropoxyethyl-4-amino-3-mercapto-5-thione-1,2,4-triazine(4,5-H).

The alkyl halides to be used as starting materials for the process according to process variant (c) are defined by the general formula (VI). Preferably, R" represents straight-chain or branched alkyl of from 1 to 3 carbon atoms. The alkyl halides are known from the literature and can also be prepared on a large industrial scale.

The following may be mentioned individually as examples of these halides-: methyl iodide, ethyl iodide, n-propyl iodide and iso-propyl iodide and the corresponding chlorides or bromides.

The process for the preparation of the compounds according to the invention in accordance with process variant (a), (b) or (c) is preferably carried out in the presence of a suitable diluent. Practically all inert organic solvents can be used for this purpose. These include, in particular, aliphatic and aromatic (optionally chlorinated) hydrocarbons, for example benzene, toluene, xylene, benzine, methylene chloride, chloroform, carbon tetrachloride and chlorobenzene; ethers, for example diethyl ether, dibutyl ether and dioxan; ketones, for example acetone, methyl ethyl ketone, methyl isopropyl ketone and methyl isobutyl ketone; nitriles, for example acetonitrile and propionitrile; and water.

Acid acceptors which can be used in process variant (c) are all customary acid-binding agents. Alkali metal carbonates and alkali metal alcoholates, such as sodium carbonate, methylate and ethylate and potassium carbonate, methylate and ethylate, have proved particularly suitable, as have aliphatic, aromatic or heterocyclic amines, for example triethylamine, trimethylamine, dimethylaniline, dimethylbenzylamine and pyridine. Process variant (a) is generally carried out in the presence of an inorganic acid. Hydrogen halide acids, such as hydrochloric acid, and sulfuric acid have proved especially suitable.

The reaction temperature can be varied within a substantial range. In general, process variants (a) and (b) are carried out at 0° to 150° C, preferably at 70° to 120° C, and the second part of process variant (c) at 0° to 80° C, preferably at 20° to 35° C.

The reaction is generally allowed to take place under normal pressure.

In carrying out process variant (a), the starting components are generally employed in the equimolar ratio. An excess of one or other component produces no significant advantages. The reaction may be carried out in one of the solvents mentioned, at the temperatures mentioned. Working up may take place in accordance with methods customary in the laboratory. In carrying out process variant (b), the sulfurizing agent may be employed in a 2-fold to 3-fold amount relative to the oxo group, and in carrying out process variant (c) the alkyl halide component may be employed in a slight excess, in most cases an excess of 3 to 5%. The reaction is preferably carried out in a solvent and in the presence of an acid acceptor, at the temperatures mentioned. Working up may take place in accordance with methods customary in the labortory.

In carrying out process variant (a), the thiocarboxylic acid amides (II), which are preferably freshly prepared, do not have to be isolated at an intermediate stage and can instead be reacted in their reaction solution.

The new compounds are obtained in a crystalline form and are characterized by their melting point.

The following examples illustrate the preparation of the instant compounds.

EXAMPLE 1

Preparation of 4-amino-6-tert.-butyl-3-methylmercapto-5-thione-1,2,4-triazine(4,5-H)

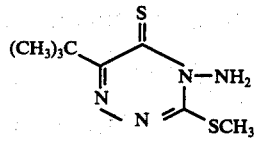

Technical-grade sodium hydroxide solution (about 35–40% strength) was added to a mixture of 147 g (0.64 mol) of 4-amino-6-tert.-butyl-3-mercapto-5-thione-1,2,4-triazine (4,5-H) and 650 ml of water, until a pH value of 11 was reached. After 5 minutes, the solution was filtered and 95 g (0.66 mol) of methyl iodide were added over the course of 1 hour. The temperature rose by about 5°–8° C and the reaction product crystallized out. The mixture was stirred further until the temperature dropped again and the product was filtered off and rinsed thoroughly with water. This gave 153 g (98% of theory) of 4-amino-6-tert.-butyl-3-methylmercapto-5-thione-1,2,4-triazine(4,5-H) in the form of a yellow powder of melting point 161° C.

EXAMPLE 2

Preparation of 4-amino-6-ethoxymethyl-3-methylmercapto-5-thione-1,2,4-triazine(4,5-H)

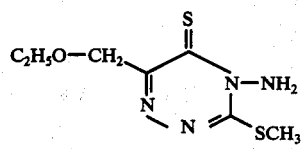

A solution of 4.5 g of sodium ethylate in ethanol was added to a solution of 14.2 g (0.065 mol) of 4-amino-6-ethoxymethyl-3-mercapto-5-thione-1,2,4-triazine(4,5-H) in 80 ml of methanol. After a short time, the sodium salt of the triazinedithione crystallized out; after adding 300 ml of ether, the salt was filtered off, dissolved in 60 ml of methanol and stirred with 9 g of methyl iodide (0.063 mol) for 15 to 20 minutes at 30° C. 150 ml of water were then added and the product was filtered off. This gave 10.5 g (70% of theory) of 4-amino-6-ethoxymethyl-3-methylmercapto-5-thione-1,2,4-triazine(4,5-H) in the form of a yellow powder of melting point 114° C.

EXAMPLE 3

Preparation of 4-amino-6-p-chlorophenyl-3-methylmercapto-5-thione-1,2,4-triazine(4,5-H)

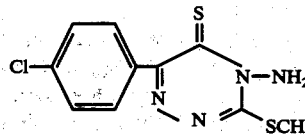

A solution of 6.1 g (0.025 mol) of S-methylthiocarbohydrazide hydroiodide in 50 ml of water was added to a solution of 10 g (0.025 mol) of p-chlorophenylglyoxylic acid N-(3-morpholinopropyl)-thioamidehydrobromide in 100 ml of hot water at 80° C. 2.5 ml of concentrated hydrochloric acid were then added and the mixture was stireed for 45 minutes at 80° C. The product which had precipitated was filtered off hot and rinsed with hot water. This gave 6.3 g (88% of theory) of 4-amino-6-p-chlorophenyl-3-methylmercapto-5-thione-1,2,4-triazine(4,5-H) in the form of a yellow powder of melting point 193° C.

EXAMPLES 4–13

The following compounds of the formula

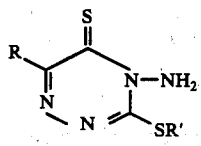

were prepared analogously to one of Examples 1 to 3:

| Example No. | R | R' | Physical data (melting point, ° C) |
|---|---|---|---|
| 4 | CH₃— | —CH₃ | 133 |
| 5 | C₂H₅— | —CH₃ | 132 |
| 6 | iso-C₃H₇— | —CH₃ | 152 |

-continued

| Example No. | R | R' | Physical data (melting point, °C) |
|---|---|---|---|
| 7 | iso-C₃H₇— | —C₂H₅ | 124 |
| 8 | (CH₃)₂CH—CH₂— | —CH₃ | 93 |
| 9 | CH₃(CH₂)₃\\CH—/C₂H₅ | —CH₃ | oily |
| 10 | 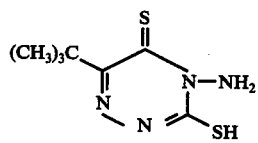 | —CH₃ | 168 |
| 11 | | —CH₃ | 144 |
| 12 | | —CH₃ | 149 |
| 13 | 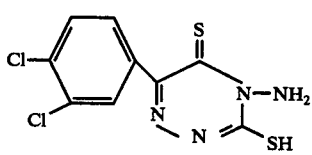 | —CH₃ | 184 |

EXAMPLE 14

Preparation of 4-amino-6-tert.-butyl-3-mercapto-5-thione-1,2,4-triazine(4,5-H)

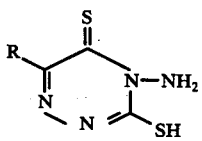

A mixture of 38.5 g (0.19 mol) of trimethylpyruvic acid N-n-butyl-thioamide, 100 ml of ethanol, 100 ml of water and 21.2 g (0.2 mol) of thiocarbohydrazide was boiled for 8 hours under reflux. After adding 300 ml of water, sodium hydroxide solution was added to the reaction mixture until the latter reacted strongly alkaline. The undissolved impurities were then extracted with ether and the aqueous phase was separated off and acidified with hydrochloric acid. The product which had precipitated was filtered off after crystallization. This gave 14 g (32% of theory) of 4-amino-6-tert.-butyl-3-mercapto-5-thione-1,2,4-triazine(4,5-H) in the form of a light brown powder of melting point 156° C.

EXAMPLE 15

Preparation of 4-amino-6-(3,4-dichlorophenyl)-3-mercapto-5-thione-1,2,4-triazine (4,5-H)

350 g (0.79 mol) of 3,4-dichlorophenylglyoxylic acid N-(3-morpholinopropyl)-thioamide hydrobromide were added to a filtered solution of 170 g (1,6 mols) of thiocarbohydrazide in 1.6 liters of hot water. Concentrated hydrochloric acid was added dropwise at 80° to 85° C until a pH value of 4 was reached (about 16 ml). The pH value was then tested every 15 minutes and kept at pH 4 by adding further hydrochloric acid. After about 3 hours, a further 56 ml of hydrochloric acid had been consumed (total amount about 72 ml = 0.8 mol) and the pH value rose no further. The product which had precipitated was filtered off hot and washed with twice 300 ml of hot water (=60° C). This gave 110 g (46% of theory) of 4-amino-6-(3,4-dichlorophenyl)-3-mercapto-5-thione-1,2,4-triazine (4,5-H) in the form of an orange powder of melting point 198° C.

EXAMPLE 16

Preparation of 4-amino-6-methyl-3-mercapto-5-thione-1,2,4-triazine (4,5-H)

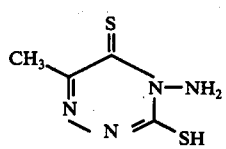

30.8 g (0.2 mol) of 3-morpholinopropylisonitrile were added dropwise to 16.5 g (0.21 mol) of acetyl chloride at 15°–20° C. After adding 200 ml of methylene chloride, hydrogen sulfide was passed into the mixture until the exothermic reaction had ended. Thereafter the solvent was distilled off in vacuo; the residue, which essentially consisted of pyruvic acid N-(3-morpholinopropyl)-thioamide hydrochloride, was dissolved in 140 ml of water and after adding a solution of 22 g (0.2 mol) of thiocarbohydrazide in 250 ml of water and 22 ml of concentrated hydrochloric acid the mixture was stirred for 1 hour at 80°–90° C. This gave 7 g (20% of theory) of 4-amino-6methyl-3-mercapto-5-thione-1,2,4-triazine (4,5-H) in the form of a yellow powder of melting point 125° C.

EXAMPLES 17-25

The following compounds of the formula were prepared analogously to one of Examples 14 to 16:

| Example No. | R | Physical data (melting point °C) |
|---|---|---|
| 17 | C₂H₅— | 127 |
| 18 | iso-C₃H₇— | 144 |
| 19 | (CH₃)₂CH—CH₂— | 58 |
| 20 | C₂H₅O—CH₂— | 190 |
| 21 | CH₃(CH₂)₃\\CH—/C₂H₅ | 120 |
| 22 | | 163 |
| 23 | | 150 |
| 24 | | 188 |

| Example No. | R | Physical data (melting point °C) |
|---|---|---|
| 25 |  | 237 |

The α-ketocarboxylic acid thioamides used as starting materials were, for example, prepared as follows:

EXAMPLE a (CH₃)₃C—CO—CS—NH—C₄H₉—n

A mixture of 33.8 g (0.2 mol) of 1,1-dichloropinacoline, 250 ml of ether, 38.4 g (1.2 g atom) of sulfur powder and 51.2 g (0.7 mol) of n-butylamine was boiled for 7 hours under reflux. The solid by-products were then filtered off and the solvent was distilled off in vacuo. This gave 38 g (95% of theory) of trimethylpyruvic acid N-n-butyl-thioamide in the form of a viscous yellow oil.

EXAMPLE b (CH₃)₃C—CO—CS—NH—CH₂—CH₂—CH₂—N⟨O⟩ × HCl 277 g (1.8 mols) of 3-morpholinopropylisonitrile were added over the course of 30–40 minutes to a solution of 217 g (1.8 mols) of pivaloyl chloride in 1 liter of methylene chloride. The temperature thereupon rose to 35° C. After the end of the addition, the reaction mixture was boiled for half an hour under reflux and was then cooled to 30° C, and about 80 g (2.35 mols) of hydrogen sulfide were passed in over the course of 3-4 hours. In the course thereof, the temperature first rose to about 40° C and then gradually fell again. Whilst the hydrogen sulfide was being passed in, the hydrochloride salt already began to crystallize out. To remove excess hydrogen sulifde, dry air was briefly blown through the solution after which the salt was filtered off and rinsed with about 100 ml of methylene chloride. This gave 343 g (62% of theory) of trimethylpyruvic acid N-(3-morpholinopropyl)-thioamide hydrochloride as an almost colorless powder of melting point 192° C.

EXAMPLE c–e

Analogously there were prepared the following compounds of the formula

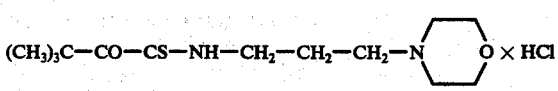

| Example | R | X | Melting point °C |
|---|---|---|---|
| c | ⟨H⟩— | Cl | 159 |
| d | Cl—⟨⟩— | Br | 193 |
| e | Cl—⟨⟩—, Cl | Br | 190 |

The active compounds according to the invention influence plant growth and can therefore be used as defoliants, desiccants, agents for potatoe halm killing, germination inhibitors and, particularly, as weed-killers. Weeds in the broadest sense are to be understood to include all plants which grow in places where they are not desired. Whether the compounds according to the invention act as total herbicides or selective herbicides depends essentially on the amount used.

The active compounds according to the invention can be used, for example, in the case of the following plants:

Dicotyledon weeds of the genera: mustard (Sinapis), cress (Lepidium), bed straw (Galium), chickweed (Stellaria), camomile (Matricaria), mayweed (Anthemis), gallant soldier (Galinsoga), goosefoot (Chenopodium), annula nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), Rotala, false pimpernel (Lindernia), dead-nettle (Lamium), speedwell (Veronica), mallow (Abutilon), emex (Emex), thornapple (Datura), violet (Viola), hamp-nettle (Galeopsis), poppy (Papaver) and knapweed (Centaurea).

Dicotyledon crops of the genera: cotton (Gossypium), soya bean (Glycine), beet (Beta), carrot (Daucus), bean (Phaseolus), pea (Pisum), potato (Solanum), flax (Linum), morning glory (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cuburbita).

Monocotyledon weeds of the genera: barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, Fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bentgrass (Apera).

Monocotyledon crops of the genera: rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the invention is in no way restricted to these genera and also extends to other plants.

The compounds may be used, depending on their concentration, for the total combating of weeds, for example on industrial terrain and railway tracks, and on paths and squares which may or may not be planted with trees. Equally, the compounds can be used to combat weeds in perennial cultures, for example in forestry and ornamental tree plantings, orchards, vineyards, citrus fruit groves, nut plantings, banana, coffee, tea, rubber, oil palm and cocoa plantations, soft fruit plantings and hop fields, and for the selective combating of weeds in annual crops.

In particular, the active compounds according to the invention are suitable for the selective combating of weeds in standing crops of cotton, cereals, soy beans and maize.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaoline, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compound according to the invention, as such or in the form of their formulations, can, in order to boost and supplement their spectrum of action in accordance with the intended use, be combined with other herbicidal active compounds, it being possible to employ ready-to-use formulations or tank mixing. In particular, the active compounds mentioned below, and other representatives of the groups of active compounds characterized by the compounds mentioned, are suitable for this purpose.

2,3,6-Trichlorobenzoic acid and its salts, 2,3,5,6-tetrachlorobenzoic acid and its salts, 3-nitro-2,5-dichlorobenzoic acid and its salts, 3-amino-2,5-dichlorobenzoic acid and its salts, 2-methoxy-3,6-dichlorobenzoic acid and its salts, 2-methoxy-3,5,6-trichlorobenzoic acid and its salts, 2,6-dichloro-thiobenzamide, 2,6-dichlorobenzonitrile, 2,4-dichlorophenoxyacetic acid and its salts and esters, 2,4,5-trichlorophenoxy-acetic acid and its salts and esters, (2-methyl-4-chlorophenoxy)-acetic acid and its salts and esters, 2-(2,4-dichlorophenoxy)-propionic acid, 2-(2-methyl-4-chlorophenoxy)-propionic acid and 2-(2,4,5-trichlorophenoxy)propionic acid and its salts and esters, 4-(2,4-dichlorophenoxy)-butyric acid and its salts and esters, 4-(2-methyl-4-chlorophenoxy)-butyric acid and its salts and esters, 2,3,6-trichlorophenyl-acetic acid and its salts, and 4-amino-3,5,6-trichloropicolinic acid.

Trichloroacetic acid and its salts, 2,2-dichloropropionic acid and its salts, 2-chloro-N,N-diallylacetic acid amide, dinitro-cresol and dinitro-sec.-butylphenol and its salts.

3-Phenyl-1,1-dimethyl-urea, 3-(4'-chlorophenyl)-1,1-dimethyl-urea, 3-(3',4'-dichlorophenyl)-1,1-dimethyl-urea, 3-(3',4'-dichlorophenyl)-1-n-butyl-1-methyl-urea, 3-(3',4'-dichlorophenyl)-1,1,3-trimethyl-urea, 3-(4'-chlorophenyl)-1-methoxy-1-methyl-urea, 3-(3'-trifluoromethyl-phenyl)-1,1-dimethyl-urea, 3-(3',4'-dichlorophenyl)-1-methoxy-1-methyl-urea, 3-(4'-bromophenyl)-1-methoxy-1-methyl-urea, 3-(3',4'-dichlorophenyl)-3-methoxy-1,1-dimethyl-urea, 3-(4'-chlorophenoxyphenyl)-1,1-dimethyl-urea, N'-cyclooctyl-N,N-dimethyl-urea, 3-(benzthiazol-2-yl)-1,3-dimethyl-urea and 3-(3-chloro-4-methylphenyl)-1,1-dimethyl-urea.

N,N-Di-(n-propyl)-S-n-propyl-thiocarbamic acid ester, N-ethyl-N-(n-butyl)-S-n-propyl-thiocarbamic acid ester, N,N-di(n-propyl)-S-ethyl-thiocarbamic acid ester, N-phenyl-O-isopropyl-carbamic acid ester, N-(m-chlorophenyl-O-isopropylcarbamic acid ester, N-(3',4'-dichlorophenyl)-O-methylcarbamic acid ester, N-(m-chlorophenyl)-O-(4-chloro-butin-2-yl)carbamic acid ester, N-(3'-methylphenyl)-O-(3methoxycarbonylaminophenyl)-carbamic acid ester and N,N-diisopropylthiocarbamic acid 2,3,3-trichloroallyl ester.

3-Cyclohexyl-5,6-trimethylene-uracil, 5-bromo-3-sec.-butyl-6-methyl-uracil, 3,6-dioxo-1,2,3,6-tetrahydropyridazine and 4-amino-5-chloro-1-phenyl-pyridazone-6.

2-Chloro-4-ethylamino-6-isopropylamino-s-triazine, 2-chloro-4,6-bis-(methoxypropylamino)-s-triazine, 2-methoxy-4,6-bis-(isopropylamino)-s-triazine, 2-diethylamino-4-isopropylacetamido-6-methoxy-s-triazine, 2-isopropylamino-4-methoxypropylamino-6-methylthio-s-triazine, 2-methylthio-4,6-bis(iso-propylamino)-s-triazine, 2-chloro-4,6-bis-(ethylamino)-s-triazine, 2-methylthio-4,6-bis(ethylamino)-s-triazine, 2-methoxy-4-ethylamino-6-isopropylamino-s-triazine, 2-methylthio-4-ethylamino-6-isopropylamino-s-triazine, 2-methoxy-4,6-bis(ethylamino)-s-triazine and 2-chloro-4,6-bis-(isopropylamino)-s-triazine.

N,N-Diethyl-2,4-dinitro-6-trifluoromethyl-1,3-phenylenediamine, N,N-di-n-propyl-2,6-dinitro-4-trifluoromethylaniline, 4'-nitro-2,4-dichloro-diphenyl ether, 3,4-dichlorophenyl-propionamide and 2',6'-diethyl-N-(methoxymethyl)-2-chloroacetanilide.

The active compounds according to the invention can be used as a mixture with other active compounds, such as fungicides, insecticides and acaricides.

The formulations in general contain 0.1 to 95 percent by weight of active compound, preferably 0.5 to 90 percent by weight. They may be diluted for actual application.

The active compounds can be employed as such or in the form of their formulations or the application forms prepared therefrom, such as ready-to-use solutions, emulsions, suspensions, powders, pastes and granules. They may be applied in the customary manner, for example by spraying, atomizing, dusting, scattering and watering.

They can be applied in accordance with either the post-emergence technique or the pre-emergence technique.

The amount of active compound employed can vary within substantial ranges. It depends essentially on the nature of the desired effect. In general, the amounts used are 0.1 to 25 kg/ha, preferably 0.25 to 10 kg/ha.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or a habitat thereof a compound according to the invention alone or in the form of a composition containing as active ingredient a compound according to the invention in admixture with a diluent or carrier.

The invention also provides crops protected from damage by weeds by being grown in areas in which, immediately prior to and/or during the time of the growing, a compound according to the invention was applied alone or in admixture with a diluent or carrier.

It will be seen that the usual methods of providing a harvested crop may be improved by the present invention.

The compounds according to the invention, and the preparation and use of the compounds according to the invention, are illustrated by the following examples.

EXAMPLE A

Post-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. The concentration of the spray liquor was so chosen that the amounts of active compound shown in the table were applied in 2,000 liters of water/ha. After 3 weeks, the degree of damage to the plants was rated in % damage in comparison to the development of the untreated control. The figures denote:

0% = no action (like untreated control)
100% = total destruction.

The active compounds, the amounts applied and the results can be seen from the table which follows:

Table A

| Active compound | kg/ha | Echino-chloa | Cheno-podium | Sinapis | Galin-soga | Stel-laria | Urtica | Oats | Cotton | Wheat |
|---|---|---|---|---|---|---|---|---|---|---|
| $C_2H_5-NH-C(=N)-N=C(SCH_3)-N=C-NH-C(CH_3)_3$ (triazine, known) | 1 | 90 | 100 | 80 | 80 | 80 | 60 | 60 | 80 | 60 |
|  | 0.5 | 80 | 80 | 80 | 40 | 80 | 60 | 40 | 40 | 40 |
|  | 0.25 | 60 | 60 | 60 | 40 | 60 | 40 | 20 | 40 | 40 |
| $(CH_3)_3C-C(=N)-N(NH_2)-C(SCH_3)=N-$ (thione triazine) | 1 | 100 | 100 | 100 | 100 | 100 | 100 | 90 | 20 | 80 |
|  | 0.5 | 80 | 100 | 100 | 100 | 100 | 100 | 80 | 0 | 60 |
|  | 0.25 | 60 | 100 | 100 | 100 | 100 | 100 | 60 | 0 | 40 |
| Phenyl-C(=N)-N(NH_2)-C(SCH_3)=N- (thione triazine) | 1 | 100 | 100 | 100 | 80 | 100 | 100 | 60 | 100 | 60 |
|  | 0.5 | 100 | 90 | 100 | 80 | 100 | 40 | 60 | 100 | 20 |
|  | 0.25 | 90 | 80 | 100 | 60 | 80 | 20 | 60 | 40 | 0 |
| $iC_3H_7-C(=N)-N(NH_2)-C(SCH_3)=N-$ (thione triazine) | 1 | 100 | 100 | 100 | 100 | 100 | 100 | 80 | 80 | 20 |
|  | 0.5 | 80 | 100 | 100 | 100 | 100 | 100 | 60 | 40 | 0 |
|  | 0.25 | 60 | 80 | 80 | 100 | 80 | 100 | 40 | 20 | 0 |

Table A-continued

| Active compound | Post-emergence Test kg/ha | Echino-chloa | Cheno-podium | Sinapis | Galin-soga | Stel-laria | Urtica | Oats | Cotton | Wheat |
|---|---|---|---|---|---|---|---|---|---|---|
| 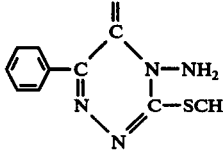 | 1 | 90 | 100 | 100 | 100 | 100 | 100 | 60 | 60 | 60 |
|  | 0.5 | 80 | 100 | 100 | 60 | 80 | 100 | 20 | 40 | 40 |
|  | 0.25 | 70 | 80 | 60 | 40 | 40 | 60 | 0 | 20 | 20 |
| 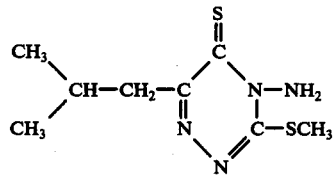 | 1 | 100 | 100 | 100 | 100 | 100 | 100 | 80 | 80 | 40 |
|  | 0.5 | 100 | 100 | 100 | 100 | 100 | 100 | 60 | 40 | 20 |
|  | 0.25 | 80 | 80 | 100 | 70 | 60 | 60 | 20 | 40 | 0 |

EXAMPLE B

Pre-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denote:

0% = no action (like untreated control)
100% = total destruction

The active compounds, the amounts applied and the results can be seen from the table which follows:

Table B
| Active compound | kg/ha | Sinapis | Echinochloa | Cheno-podium | Pre-emergence Test Lolium | Stellaria | Galinsoga | Matricaria | Avena fatua | Cotton | Wheat | Soya | Maize |
|---|---|---|---|---|---|---|---|---|---|---|---|---|
| 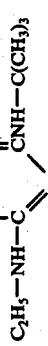 C₂H₅—NH—C ... CNH—C(CH₃)₃ (known) | 2.5 1.25 | 90 80 | 80 80 | 100 100 | 60 40 | 100 100 | 100 80 | 80 80 | 40 0 | 40 40 | 0 0 | 60 40 | 40 0 |
| 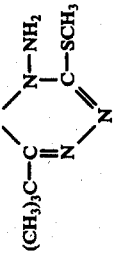 (CH₃)₃C— ... | 2.5 1.25 | 100 100 | 90 80 | 100 100 | 100 90 | 100 100 | 100 100 | 100 90 | 90 70 | 20 0 | 20 0 | 40 20 | 20 0 |
| 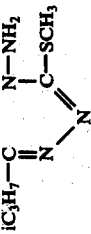 iC₃H₇— ... | 2.5 1.25 | 100 90 | 100 80 | 100 100 | 100 90 | — — | 100 100 | 100 80 | 90 80 | 40 20 | 80 60 | 20 0 | 60 40 |
| 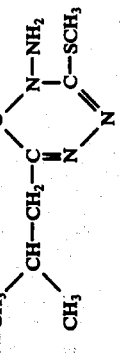 CH₃—CH—CH₂— CH₃ ... | 2.5 1.25 | 100 100 | 60 60 | 100 100 | 100 90 | 100 100 | 100 100 | 100 100 | 60 40 | 20 0 | 60 40 | 40 20 | 20 0 |

It will be appreciated that the instant specification and examples are set forth by way of illustration and not limitation, and that various modifications and changes may be made without departing from the spirit and scope of the present invention.

What is claimed is:

1. 4-Amino-5-thione-1,2,4-triazine (4,5-H) compound of the formula

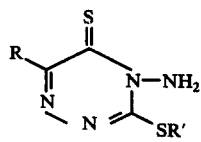

in which

R is alkyl of up to 8 carbon atoms; cycloalkyl of 5 to 7 carbon atoms; cycloalkenyl of 5 to 7 carbon atoms; phenyl, which can optionally be mono-substituted or polysubstituted by halogen; or alkoxyalkyl of 1 to 4 carbon atoms per alkyl and alkoxy moiety; and R' is hydrogen or alkyl of up to 4 carbon atoms.

2. 4-Amino-5-thione-1,2,4-triazine (4,5-H) compound as claimed in claim 1 wherein R is alkyl of up to 8 carbon atoms.

3. 4-Amino-5-thione-1,2,4-triazine (4,5-H) compound as claimed in claim 1 wherein R is cycloalkyl of from 5 to 7 carbon atoms.

4. 4-Amino-5-trione-1,2,4-triazine (4,5-H) compound as claimed in claim 1 wherein R is cycloalkenyl of from 5 to 7 carbon atoms.

5. 4-Amino-5-thione-1,2,4-triazine (4,5-H) compound as claimed in claim 1 wherein R is phenyl of from 1 to 4 carbon atoms.

6. 4-Amino-5-thione-1,2,4-triazine (4,5-H) compounds as claimed in claim 1 wherein R is halophenyl of up to 4 carbon atoms.

7. 4-Amino-5-thione-1,2,4-triazine (4,5-H) compound as claimed in claim 1 wherein R is alkoxyalkyl of up to 4 carbon atoms per alkyl and alkoxy moiety.

8. 4-Amino-5-thione-1,2,4-triazine (4,5-H) compound as claimed in claim 1 wherein R' is hydrogen.

9. 4-Amino-5-thione-1,2,4-triazine (4,5-H) compound as claimed in claim 1 wherein R' is alkyl of up to 4 carbon atoms.

10. 4-Amino-5-thione-1,2,4-triazine (4,5-H) compound as claimed in claim 1 designated 4-amino-6-tert.-butyl-3-methylmercapto-5-thione-1,2,4-triazine (4,5-H).

11. 4-Amino-5-thione-1,2,4-triazine (4,5-H) compound as claimed in claim 1 designated 4-amino-6-cyclohexyl-3-methylmercapto-5-thione-1,2,4-triazine (4,5-H).

12. 4-Amino-5-thione-1,2,4-triazine (4,5-H) compound as claimed in claim 1 designated 4-amino-6-isopropyl-3-methylmercapto-5-thione-1,2,4-triazine (4,5-H).

13. 4-Amino-5-thione-1,2,4-triazine (4,5-H) compound as claimed in claim 1 designated 4-amino-6-phenyl-3-methylmercato-5-thione-1,2,4-triazine (4,5-H).

14. 4-Amino-5-thione-1,2,4-triazine (4,5-H) compound as claimed in claim 1 designated 4-amino-6-isobutyl-3-methylmercapto-5-thione-1,2,4-triazine (4,5-H).

* * * * *